US005237618A

United States Patent [19]

Bethel

[11] Patent Number: 5,237,618

[45] Date of Patent: Aug. 17, 1993

[54] ELECTRONIC COMPENSATION SYSTEM FOR ELIMINATION OR REDUCTION OF INTER-CHANNEL INTERFERENCE IN NOISE CANCELLATION SYSTEMS

[75] Inventor: Lawrence L. Bethel, Shirley, Mass.

[73] Assignee: General Electric Company, Schenectady, N.Y.

[21] Appl. No.: 522,144

[22] Filed: May 11, 1990

[51] Int. Cl.[5] .......... A61F 11/06; H04R 3/02; H04B 15/00

[52] U.S. Cl. .......... 381/71; 381/73.1; 381/93; 381/94

[58] Field of Search .......... 381/71, 73.1, 93, 94, 381/10, 13, 1

[56] References Cited

U.S. PATENT DOCUMENTS

| | | | |
|---|---|---|---|
| 4,052,720 | 10/1977 | McGregor | 381/73.1 |
| 4,356,349 | 10/1982 | Robinson | 381/1 |
| 4,394,537 | 7/1983 | Shima et al. | 381/1 |
| 4,449,235 | 5/1984 | Swigert | 381/71 |
| 4,473,906 | 9/1984 | Warnaka et al. | 381/71 |
| 4,480,333 | 10/1984 | Ross | 381/71 |
| 4,490,841 | 12/1984 | Chaplin et al. | 381/71 |
| 4,550,423 | 10/1985 | Naito | 381/13 |
| 4,566,118 | 1/1986 | Chaplin et al. | 381/71 |
| 4,589,133 | 5/1986 | Swinbanks | 381/71 |
| 4,596,033 | 6/1986 | Swinbanks | 381/71 |
| 4,677,677 | 6/1987 | Eriksson | 381/71 |
| 4,689,821 | 8/1987 | Salikuddi | 381/94 |
| 4,723,294 | 2/1988 | Taguchi | 381/94 |
| 4,783,817 | 11/1988 | Hamada et al. | 381/71 |
| 4,815,141 | 3/1989 | Carver | 381/94 |
| 4,829,590 | 5/1989 | Ghose | 455/61 |
| 4,862,506 | 8/1989 | Langarten | 381/71 |
| 4,932,063 | 6/1990 | Nakamura | 381/94 |
| 4,956,867 | 9/1990 | Zurek et al. | 381/94 |

FOREIGN PATENT DOCUMENTS

| | | | |
|---|---|---|---|
| 0071947 | 2/1983 | European Pat. Off. . | |
| 2222053A | 2/1990 | United Kingdom | 381/71 |

OTHER PUBLICATIONS

Peterson et al.—Multimicrophone Adaptive Beamforming for Interference Reduction in Hearing Aid, Nov. 1986, Journal of Rehabilitation and Development.

Peterson—Using Linearly-Constrained . . . Reverberation Rooms, Apr. 1987, IEEE.

Griffiths et al.—An Alterative Approach to Linearly Constrained Adaptive Beamforming, Jan. 1982, IEEE.

Master of Science Thesis, Massachusetts Institute of Technology, "The Design and Analysis of An Actively Augmented Vibration Isolation System Using Classical and Linear Quadratic Feedback Control Techniques" by Martha Elizabeth Demeo, Sep. 1988 (CSDL-T-1008).

*Primary Examiner*—James L. Dwyer
*Assistant Examiner*—Jack Chiang
*Attorney, Agent, or Firm*—Nixon & Vanderhye

[57] ABSTRACT

Compensation for interaction between separate channels of a noise cancellation system in a vibrating or noisy structure is obtained by the addition of pre- and post-processing circuits for channel controllers to electronically separate the channels so that each channel operates on uncoupled modes of vibration. The processing circuits include sum and difference elements.

17 Claims, 3 Drawing Sheets

ELECTRONIC COMPENSATION SYSTEM FOR ELIMINATION OR REDUCTION OF INTER-CHANNEL INTERFERENCE IN NOISE CANCELLATION SYSTEMS

FIELD OF THE INVENTION

The invention relates to noise cancellation systems wherein an introduced noise is controlled and combined with the original system noise such that cancellation of both the original and introduced noises is substantially obtained.

BACKGROUND AND SUMMARY OF THE INVENTION

Physical electromechanical structures particularly large rotating machines such as turbine generators and propulsion drive units generate unwanted noise or vibrations involving both rotational and translatory motion. Various methods and structures have been used in the past to reduce, isolate or eliminate such undesirable vibration signals.

It has been known, for example, to isolate vibrations by way of passive restraint systems such as resilient mounts, springs, the addition of large masses or dampening devices such as shock absorbers and the like. Such passive systems have varied from simple to complex but have normally added substantially to the weight and mass of a system.

Active noise suppression or cancellation systems have also been known and used in the prior art. Such systems are known to be relatively small and light with respect to passive noise suppression or cancellation systems but are normally far more complex than the passive systems. Such active systems, for example, normally operate by introducing a noise into the vibrating or noisy structure as an additional noise to that which exists in the system. Such introduced noise is carefully controlled so that the original and induced noises will combine in such a manner as to obtain cancellation through destructive interference. The process is performed by measuring noise or vibration signals from one or more sensing devices and in accordance with an analysis of the sensed noise adding the exactly opposite noise through a like number of actuation devices to obtain a net reduction or substantial cancellation of system noise. Such noise cancellation or nulling systems typically involve a plurality of separate channels wherein each channel includes a sensor and an actuator.

I have discovered, however, that a difficulty arises in such systems since there is often an interaction between the separate channels. That is to say, commercially available control systems for noise cancellation principally operate as single channel controllers wherein for each such channel there is a single input and a single output signal. Under many conditions the individual channels interact and result in an unstable condition in which excessively large and potentially damaging signals are produced by the system to be controlled. For example, where strong interaction between channels occurs, the noise required to silence one channel may interact with another channel and increase the noise of the latter channel. Such a condition can cause the control system to erroneously increase the induced or compensating noise in certain channels while minimizing the noise in others. Moreover, such unstable systems may operate repetitively in such a manner and thus result in higher and higher noise as well as system damage.

It is, therefore, the principle object of the present electronic compensation system to provide a means for electronically separating the channels and allowing the noise cancellation system to operate as intended.

It is a further object of the disclosed system to provide a means and method of electronically combining the signals from two or more interacting channels in such a manner as to create new channels which do not interact but which allow the existing control systems to operate effectively in applications and environments in which they were previously ineffective.

It is a still further object of the exemplary embodiments disclosed herein to provide a means and manner for combining the signals of the parallel channels of commercially available noise cancellation control systems that are not stable under certain conditions so that such channels are decoupled as to the modes of vibration of a structure in such manner as to maintain stability.

It is a still further object of the disclosed inventive subject matter to provide an electronic compensation system and method wherein signals from multiple input sensors are preprocessed for connection to the control system as well as being additionally processed prior to their connection with the noise injecting actuators. The compensation network includes active devices for combining two or more signals into a single signal wherein the single signal would be then processed by the control system to generate an anti-noise control channels is then passed through post-processing compensation steps before being fed to two or more anti-noise signal injecting actuators.

These and further objects and advantages of the present invention will become more apparent upon reference to the following specification, appended claims and drawings.

DETAILED DESCRIPTION OF THE DRAWINGS

Figure 1:
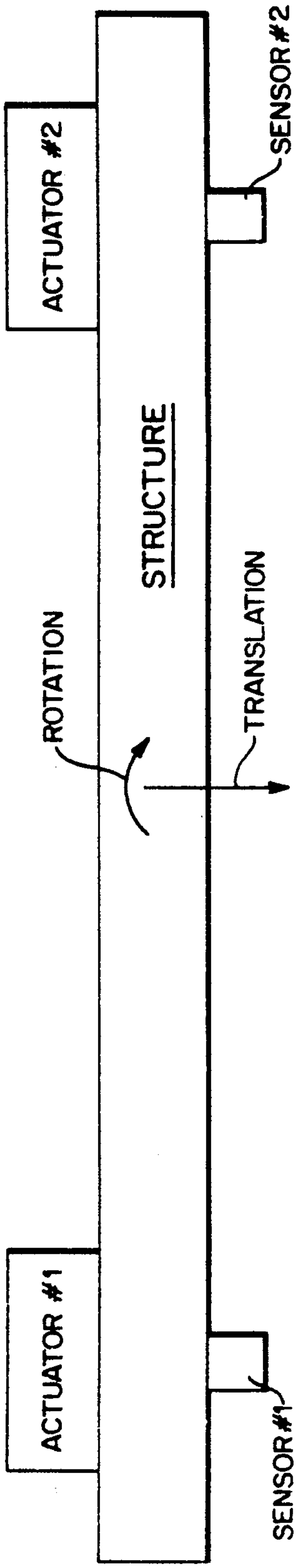
FIG. 1 is representative of a physical machine structure as well as illustrating the placement of vibration sensing devices and anti-noise signal injecting actuators.

As generally shown in FIG. 1, a noisy machine structure such as rotating equipment as found in turbine or motor generator sets exists wherein the sensors and actuators of a two-channel noise cancellation system are included. Although the block diagram of FIG. 1 does not illustrate the source of the noise or the manner of support of the structure (which may include passive noise suppression devices such as resilient mountings or the like), the structure is sufficient to illustrate a conventional two-channel noise cancellation system installation including representations of vibratory motion of a selected translatory direction as well as vibratory motion of a rotational nature about a principle axis of the body. The installation would typically include sensors placed in such a manner as to measure noise or vibration at points of interest on the structure such as vibrations producing a rotational motion about a selected axis and/or translational motion along a selected axis. Such sensors may be mechanical or electromechanical including piezoelectric accelerometers such as Wilcoxon Model Nos. 793 UF which are conventionally used for detecting vibrations and the like.

The actuators illustrated in FIG. 1 are typically electromagnetic shakers such as Wilcoxon F4's or F10's and are also conventionally placed at points of interest on the structure. Said points of interest are various locations selected in order to put or induce the anti-noise signals into the system and are usually near the respective sensors.

Figure 2:
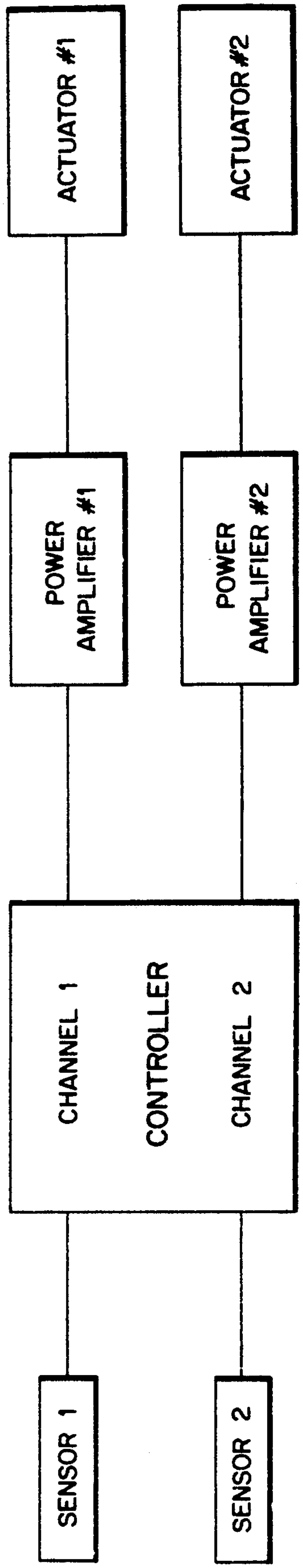
FIG. 2 (PRIOR ART)
FIG. 2 illustrates in block diagram form a typical prior art noise suppression or cancellation system utilizing commercially available elements in the parallel channels of the system.

FIG. 2 illustrates a conventional plural channel noise cancellation system wherein the vibrations sensed by each sensor are transmitted to a channel controller such as a NCT Model 2000-8 for the purpose of applying a transfer function to the input signal wherein the transfer function would be such as to produce an anti-noise signal which when combined with the sensed vibrations or noise would substantially cancel the noise by way of destructive interference. As may be seen in FIG. 2, the anti-noise signal produced by the controller for each channel is thereafter amplified and applied to the machine structure by way of an electromagnetic actuator. As previously indicated, in such conventional systems, each channel operates in an independent manner and does not take into account the effect of one actuator on the other channel. When such signals are applied to structures such as rotary equipment or even simple structures such as rigid bodies, the system is often unstable due to the interaction between channels.

Figure 3:
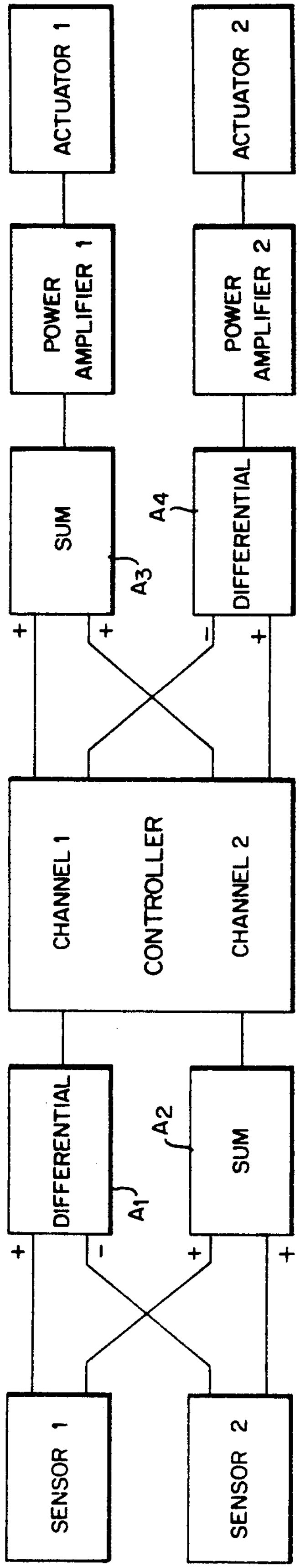
FIG. 3 is an exemplary embodiment of my improved noise cancellation system illustrating the addition of the compensation system.

An exemplary embodiment of my improved system which includes an electronic compensation system is illustrated in FIG. 3. This exemplary embodiment includes a preprocessing section comprising differential amplifier A1 and summing amplifier A2 whereby the difference signal produced by amplifier A1 is a signal which is proportional to the rotational motion of the FIG. 1 structure about the selected rotation axis. This rotational motion signal is used as an input to the first channel of the controller which applies a transfer functional in the conventional manner.

Similarly, the summing amplifier A2 passes the sum of the signals developed by the sensors wherein the signal passed to the second channel of the controller is proportional to the translatory motion of the body, and thus, the modes of vibration from channel to channel are decoupled.

Subsequent to the application of the controller transfer function to the input sum and difference signals, the output of both the first or rotational channel and the second or translational channel are split and passed to sum and difference amplifiers A3 and A4 in the manner indicated in FIG. 3. As further indicated in the FIG. 3 post-processing section, one of the rotational channel outputs is inverted by a phase change before amplification by power amplifier 2. As such, the two power amplifiers drive the actuators in anti-phase which would produce only rotational motion or anti-noise signals. The second channel of control, however, is passed to both amplifier channels without inversion. Accordingly, both actuators would be driven in unison and would produce only translatory motion.

The motions or vibrations introduced by the actuators, of course, would be induced anti-noise signals or vibrations which by way of destructive interference cancel or substantially cancel the vibrations detected by the sensors. However, the pre- and post-processing sections would uncouple of the motions and, therefore, prevent the interaction between the prior art channels, and achieve stable operation under a wide variety of conditions.

Figure 4:
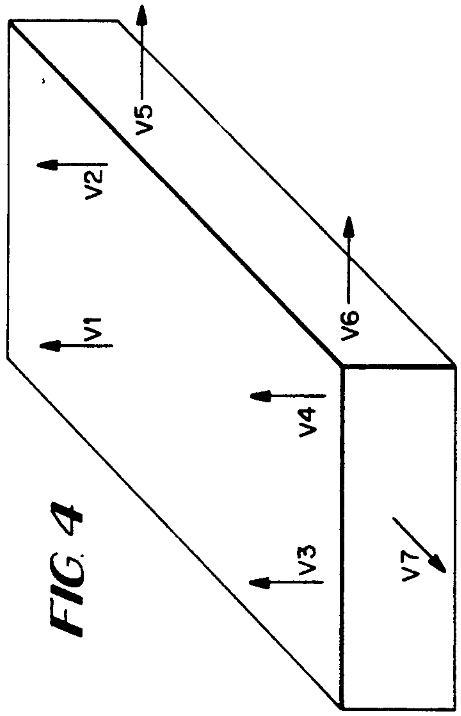
FIG. 4 illustrates a sensor and actuator placement geometry for controlling six modes of machine structure motion.
Figure 4A:
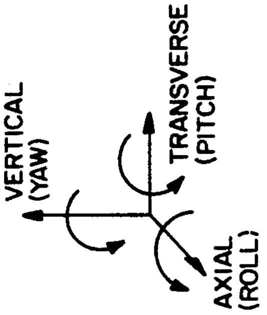
FIG. 4A illustrates in a generalized manner the six modes of rigid body motion sensed and controlled.

Although the electronic compensation circuitry illustrated in FIG. 3 which has been provided so as to electronically separate the channels so that the vibrations or motions may be controlled in an uncoupled manner, has been illustrated using two channels, additional channels and vibrational modes may also be included in the system and be decoupled in a manner similar to that described above. For example, as generally illustrated in FIGS. 4 and 4A six modes of vibration or noise may be sensed by a set of seven accelerometers, four of which would be oriented to measure the vertical as well as pitch and roll motions. As further illustrated in FIGS. 4 and 4A, two of the sensors would be oriented laterally to measure translation in a transverse direction as well as yaw motion with the seventh accelerometer measuring axial motion. Both the sensors and actuators would be positioned in the locations indicated by inputs V1 through V7 in FIG. 4.

Figure 5:
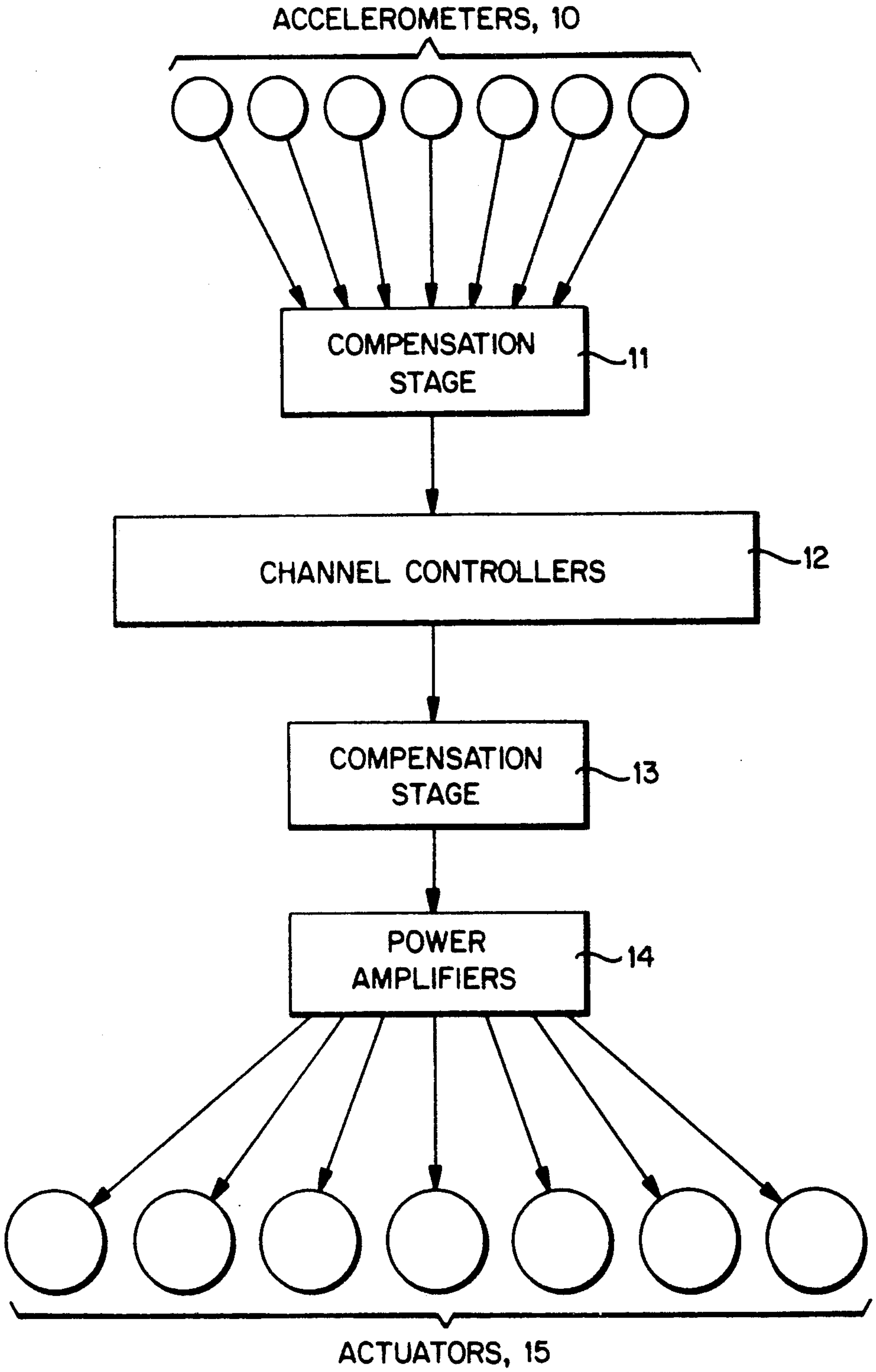
FIG. 5 is a block diagram of the improved system for controlling six modes of vibration.

As illustrated in FIG. 5, the seven accelerometer sensors 10 may be connected to a multi-channel controller 12 through a compensation or preprocessing stage 11. The preprocessing stage may include six instrument amplifiers to buffer and invert the inputs wherein the output stages may be summed through the use of resistances in such a manner as to produce the following six uncoupled modes of vibration through the use of seven inputs.

$$Vv=(V1+V2+V3+V4)/4.0 \quad (1)$$

$$Vp=(V1+V2-V3-V4)/4.0 \quad (2)$$

$$Vr=(-V1+V2-V3+V4)/4.0 \quad (3)$$

$$Vt=(V5+V6)/2.0 \quad (4)$$

$$Vy=(-V5+V6)/2.0 \quad (5)$$

$$Va=V7 \quad (6)$$

where

Vv=Vertical Control Input
Vp=Pitch Control Input
Vr=Roll Control Input
Vt=Transverse Control Input
Vy=Yaw Control Input
Va=Axial Control Input The uncoupled modes are each input to a channel controller for the application of transform functions and thereafter connected to compensation or a post-processing stage 13 which is similar to the preprocessing stage but is for the purpose of producing seven individual actuator outputs from the six controller outputs in accordance with the following:

$$V1=(Vv+Vp-Vr)/3.0 \quad (7)$$

$$V'2=(V'v+V'p+V'r)/3.0 \quad (8)$$

$$V'3=(V'v-V'p-V'r)/3.0 \quad (9)$$

$$V'4=(V'v-V'p+V'r)/3.0 \quad (10)$$

$$V'5=(V't-V'y)/2.0 \quad (11)$$

$$V'6=(V't+V'y)/2.0 \quad (12)$$

$$V'7=V'a \quad (13)$$

where

V'v=Vertical Control Output
V'p=Pitch Control output
V'r=Roll Control Output
V't=Transverse Control Output
V'y=Yaw Control Output
V'a=Axial Control Output Thus, it may be seen that the geometry addressed in the specification, although specifically illustrating two and six decoupled modes of vibration, is sufficient to indicate that it would be obvious to those skilled in the art that other geometries may be addressed using a similar technique. Such geometries may include greater and fewer channels of control than that which is illustrated in FIG. 5, for example and may include flexible body modes as well as rigid body modes.

As illustrated in the drawings, the operation of the system contemplates the use of symmetric bodies wherein the sensors and actuators are symmetrically placed, and, therefore, the relationship between channels is known and constant. The teachings of my invention, however, may also be applied to non-symmetric bodies by way of varying the gains in the summing and differential amplifiers. Additionally, the principles of this invention can be applied to bending or non-rigid as well as rigid bodies.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A method of separating and controlling interacting signals in a multichannel noise cancellation system of a noisy structure, said method comprising steps of:

sensing and generating signals representative of vibrations of said structure at a plurality of position;

combining said signals with same vibration direction representative of vibrations at a plurality of positions to produce a plurality of second signals, each said second signal corresponding substantially only to sensed vibratory motion of a given translatory or rotational direction;

applying each of said second signals to a separate channel;

applying a control function to each of said second signals, and in response thereto causing generation of third signals which when applied to said structure combine with and cancel said structure vibrations.

2. The method of claim 1 wherein the step of causing the generation of said third signals further includes a step of obtaining sum and difference of fourth signals that are produced by applying said control function to each said second signal whereby said third signals include anti-phase signals for introducing rotational motion noise into said structure.

3. The method of claim 2 wherein said third signals when applied to said structure also include translatory motion noise which along with said rotational motion noise destructively interferes with and substantially cancels said structure vibrations.

4. The method of claim 1 wherein the step of combining comprises the step of obtaining the sum and difference signals of the sensed vibration so as to produce said plurality of second signals.

5. The method of claim 1 wherein said third signals are applied to said structure by vibration inducing actuators.

6. The method of claim 1 wherein said third signals are amplified prior to being applied to said structure.

7. A noise cancellation system for use with a vibration producing machine structure, said system including plural channels, each channel including a vibration sensing and signal generating means, a channel controller for producing output anti-noise signals and an actuator for introducing anti-vibration signals into the machine structure, the improvement comprising:

a compensation means for processing the sensed vibrations and said anti-noise signals said compensation means being connected to each channel so that signals from said sensing and signal generating means applied to said channel controller are separated as to machine stricture vibrations of different directions to prevent interaction between channels and said anti-vibration signals are applied to the machine structure and decrease the machine structure vibrations.

8. The improved noise cancellation system of claim 7 wherein said compensation means includes:

a preprocessing means connected to each said sensing and signal generating means for producing and supplying a signal to said channel controller, wherein said supplied signals correspond substantially only to sensed vibratory motion of either a given translatory or a rotational direction.

9. The improved noise cancellation system of claim 8 wherein said compensation means further includes:

post-processing means connected between said channel controller outputs and said actuators for driving at least two of the actuators in anti-phase to compensate for machine vibrations of a given rotational direction and for driving at least two of said actuators in unison to compensate for translatory motion of a given direction.

10. The improved system of claim 8 wherein the signals produced and supplied by said preprocessing means are proportional to the sensed translatory and rotational motions of said machine structure.

11. The improved system of claim 9 wherein said preprocessing and post-processing means include sum and difference means.

12. The improved system of claim 9 further including amplifier means connected to said post-processing means for driving said at least two actuators.

13. A noise cancellation system for use with a vibration producing machine structure, said system comprising:

means in each of a plurality of channels for sensing the vibrations of the machine structure and for producing signals corresponding to the sensed vibrations;

means in each channel for combining the signals with same vibration direction corresponding to the sensed vibrations to produce uncoupled motion signals which substantially correspond only to vibratory motion of given translatory or rotational directions;

means in each channel responsive to the means for combining for separately controlling each of the signals produced by said means for combining to produce anti-vibration signals which when applied to said machine structure destructively interfere with and substantially cancel said structure vibrations.

14. The system of claim 13 further including actuator means in each channel for applying said anti-vibration signals to said machine structure.

15. The system of claim 14 wherein said means for controlling further includes:

a means for applying a transform function to each channel receiving one of said uncoupled motion signals; and means responsive to said means for applying for producing said anti-vibration signals, said anti-vibration signals including signals corresponding to rotational motion of said given direction and inverted such signals corresponding to rotational motion, said anti-vibration signals also including signals corresponding to translational motion of said given directions.

16. The system of claim 15 wherein said means for producing further include sum and difference means.

17. The system of claim 15 wherein said means for producing include amplifier means connected thereto for driving said actuator means.

* * * * *